United States Patent
Wang et al.

(10) Patent No.: US 7,639,354 B2
(45) Date of Patent: Dec. 29, 2009

(54) RAMAN SIGNAL-ENHANCING STRUCTURES FOR RAMAN SPECTROSCOPY AND METHODS FOR PERFORMING RAMAN SPECTROSCOPY

(75) Inventors: Shih-Yuan Wang, Palo Alto, CA (US); Zhiyong Li, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 421 days.

(21) Appl. No.: 11/701,045

(22) Filed: Jan. 31, 2007

(65) Prior Publication Data
US 2008/0180662 A1    Jul. 31, 2008

(51) Int. Cl.
*G01J 3/44* (2006.01)

(52) U.S. Cl. ..................................... 356/301

(58) Field of Classification Search ................. 356/301
See application file for complete search history.

(56) References Cited

U.S. PATENT DOCUMENTS

| | | | |
|---|---|---|---|
| 7,359,048 B2 * | 4/2008 | Wang et al. | 356/301 |
| 2002/0142480 A1 * | 10/2002 | Natan | 356/301 |
| 2006/0056463 A1 * | 3/2006 | Wang et al. | 372/3 |
| 2007/0252982 A1 * | 11/2007 | Wang et al. | 356/301 |

* cited by examiner

*Primary Examiner*—Kara E Geisel (57) ABSTRACT

Raman systems include a radiation source, a radiation detector configured to detect Raman scattered radiation, and a Raman signal-enhancing structure. The Raman signal-enhancing structure includes a first layer of Raman signal-enhancing material, a substantially monomolecular layer of molecules disposed on at least a portion of the first layer of Raman signal-enhancing material, and a second layer of Raman signal-enhancing material disposed on at least a portion of the substantially monomolecular layer of molecules. The second layer of Raman signal-enhancing material is disposed on a side of the layer of molecules opposite the first layer of Raman signal-enhancing material. Methods of performing Raman spectroscopy include providing such a Raman signal-enhancing structure, providing an analyte on the Raman signal-enhancing structure, irradiating the analyte and the structure, and detecting Raman scattered radiation.

19 Claims, 7 Drawing Sheets

Figure 1:
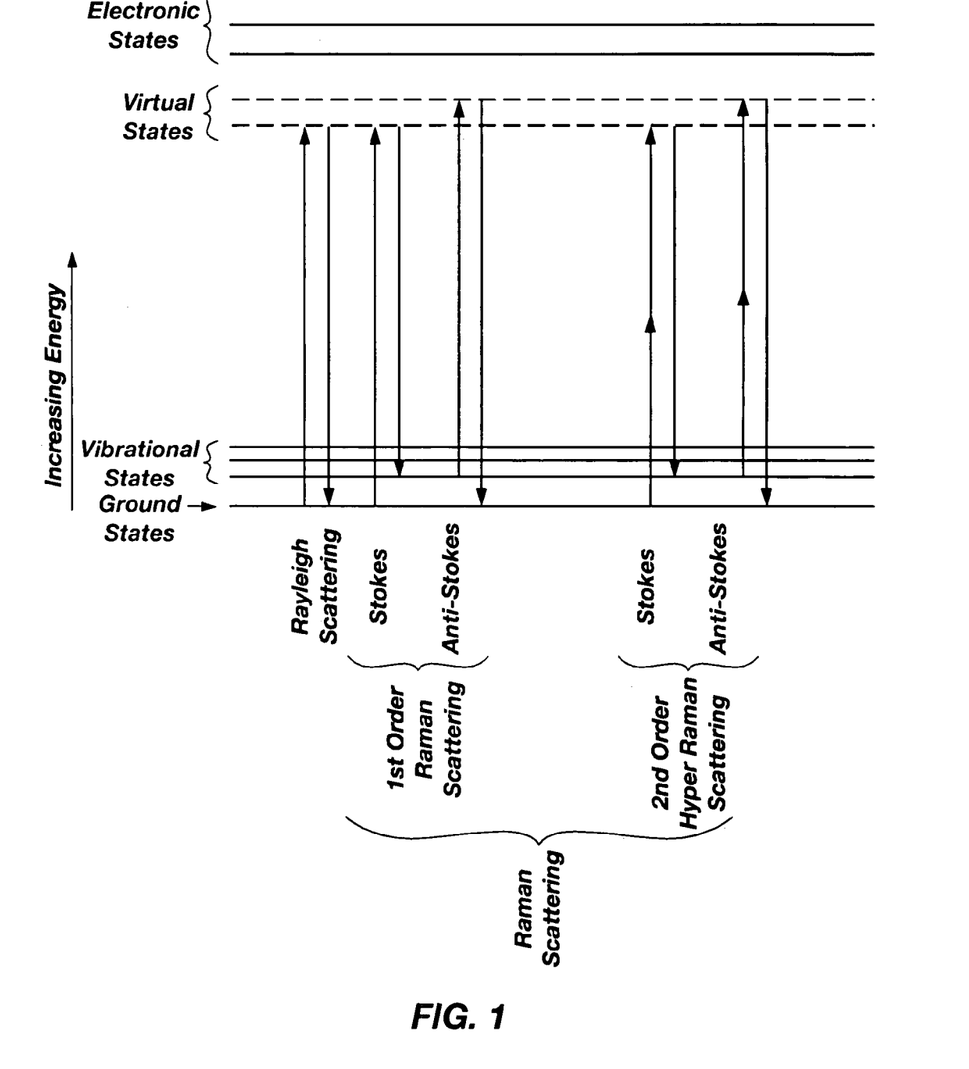
FIG. 1 is a Jablonski energy level diagram schematically representing Rayleigh and Raman scattering processes for a hypothetical analyte.

FIG. 12 ically in FIG. 1, which illustrates various energy levels of a hypothetical analyte. In FIG. 1, energy levels of the analyte are represented as horizontal lines. As seen therein, the ground state energy level (the lowest energy level) is shown at the bottom of the diagram, excited vibrational energy states are shown just above the ground state, excited electronic energy states are shown at the top of the diagram, and virtual excited states are shown between the excited electronic states and the excited vibrational states. As seen in FIG. 1, Rayleigh scattering typically involves absorption of a single photon of the incident radiation by the analyte, which causes the analyte to transition from the ground state to a virtual state followed by relaxation to the ground state. As the analyte relaxes to the ground state, the analyte emits a photon of scattered radiation that has energy equal to that of the photon of the incident radiation. In this manner, the photon of the incident radiation is considered to have been elastically scattered.

RAMAN SIGNAL-ENHANCING STRUCTURES FOR RAMAN SPECTROSCOPY AND METHODS FOR PERFORMING RAMAN SPECTROSCOPY

FIELD OF THE INVENTION

The present invention relates to Raman spectroscopy. More particularly, the invention relates to Raman signal-enhancing structures for enhancing the Raman scattered radiation that is scattered by an analyte, Raman spectroscopy systems including such Raman signal-enhancing structures, and methods for performing Raman spectroscopy using such Raman signal-enhancing structures.

BACKGROUND OF THE INVENTION

Raman spectroscopy is a technique for analyzing molecules or materials. In conventional Raman Spectroscopy, an analyte (or sample) that is to be analyzed is irradiated with high intensity monochromatic electromagnetic radiation provided by a radiation source, such as a laser. An electromagnetic radiation detector detects radiation that is scattered by the analyte. The characteristics of the scattered radiation provide information relating to the analyte.

Conventional Raman spectroscopy systems typically include an electromagnetic radiation source that is configured to emit incident electromagnetic radiation, an analyte stage on which an analyte may be positioned, and an electromagnetic radiation detector. The radiation detector is configured to detect at least a portion of scattered radiation that is scattered by the analyte. Raman spectroscopy systems also typically include various optical components positioned between the radiation source and the analyte stage, and between the analyte stage and the radiation detector. Such optical components may include lenses, filters, and apertures.

The radiation source may be a commercially available laser. The wavelength or wavelengths of incident electromagnetic radiation that may be emitted by the electromagnetic radiation source typically are within or near the visible region of the electromagnetic radiation spectrum.

The radiation detector receives and detects at least a portion of the scattered radiation that is scattered by an analyte disposed on the analyte stage. The detector may include a device for determining the wavelength of the scattered radiation (for example, a monochromator) and a device for determining the intensity of the scattered radiation (for example, a photomultiplier). Typically, the scattered radiation is scattered in all directions relative to the analyte stage.

Optical components positioned between the radiation source and the analyte stage are used to collimate, filter, or focus the incident radiation before the incident radiation impinges on the analyte stage. Optical components positioned between the analyte stage and the radiation detector are used to collimate, filter, or focus the scattered radiation.

An analyte may be provided on an analyte stage of a Raman spectroscopy system and irradiated with incident radiation emitted by a radiation source to perform Raman spectroscopy using a Raman spectroscopy system. As the incident radiation impinges on the analyte, at least some of the incident radiation will be scattered by the analyte. A majority of the photons of the incident radiation that impinge on the analyte are elastically scattered by the analyte. In other words, the scattered photons have the same energy, and thus the same wavelength, as the incident photons. This elastic scattering of photons is termed "Rayleigh scattering," and radiation consisting of these elastically scattered photons is termed "Rayleigh scattered radiation" or "Rayleigh radiation."

The Rayleigh scattering process can be further described with reference to the simplified Jablonski diagram shown schematically in FIG. 1, which illustrates various energy levels of a hypothetical analyte. In FIG. 1, energy levels of the analyte are represented as horizontal lines. As seen therein, the ground state energy level (the lowest energy level) is shown at the bottom of the diagram, excited vibrational energy states are shown just above the ground state, excited electronic energy states are shown at the top of the diagram, and virtual excited states are shown between the excited electronic states and the excited vibrational states. As seen in FIG. 1, Rayleigh scattering typically involves absorption of a single photon of the incident radiation by the analyte, which causes the analyte to transition from the ground state to a virtual state followed by relaxation to the ground state. As the analyte relaxes to the ground state, the analyte emits a photon of scattered radiation that has energy equal to that of the photon of the incident radiation. In this manner, the photon of the incident radiation is considered to have been elastically scattered.

In addition to the Rayleigh scattering of photons, a very small fraction of the photons of the incident radiation may be inelastically scattered by the analyte. Raman scattered radiation is also emitted from the analyte. Typically, only about 1 in $10^7$ of the photons of the incident radiation is inelastically scattered by the analyte. These inelastically scattered photons have a different wavelength than the photons of the incident radiation. This inelastic scattering of photons is termed "Raman scattering," and radiation consisting of Raman scattered photons is termed "Raman scattered radiation" or "Raman radiation." The photons of the Raman scattered radiation can have wavelengths less than, or more typically, greater than the wavelength of the photons of the incident radiation.

The Raman scattering process can be further described with reference to the simplified Jablonski diagram shown in FIG. 1. When a photon of the incident radiation collides with the analyte, energy can be transferred from the photon to the analyte or from the analyte to the photon. When energy is transferred form the photon of the incident radiation to the analyte, the Raman scattered photon will have a lower energy and a corresponding longer wavelength than the incident photon. These Raman scattered photons having lower energy than the incident photons are collectively referred to in Raman spectroscopy as the "Stokes radiation." As seen in FIG. 1, 1st order Stokes Raman scattering typically involves absorption of a single photon of the incident radiation by the analyte, which causes the analyte to transition from a first energy state (for example, the ground state) to an excited virtual state. The analyte then relaxes to an excited vibrational state of higher energy than the first energy state. As the analyte relaxes to the excited vibrational state, the analyte emits a photon of scattered radiation that has less energy (and a longer wavelength) than the photon of the incident radiation. In this manner, the photon of the incident radiation is considered to have been inelastically scattered.

When energy is transferred from the analyte to a Raman scattered photon, the Raman scattered photon will have a higher energy and a corresponding shorter wavelength than the photon of the incident radiation. These Raman scattered photons, which have higher energy than the incident photons, are collectively referred to in Raman spectroscopy as the "anti-Stokes radiation." As seen in FIG. 1, 1st order anti-Stokes Raman scattering typically involves absorption of a single photon of the incident radiation by the analyte, which causes the analyte to transition from an excited vibrational energy state to an excited virtual state. The analyte then relaxes to a lower energy state (for example, the ground state) than the excited vibrational energy state. As the analyte relaxes to the lower energy state, the analyte emits a photon of scattered radiation that has more energy (and a shorter wavelength) than the photon of the incident radiation. In this manner, the photon of the incident radiation is considered to have been inelastically scattered.

The shift in energy (wavelength, frequency, or wave number) of the Raman scattered photons in relation to the Rayleigh scattered photons is known as the "Raman shift."

Raman scattering primarily involves a one photon excitation—one photon relaxation process. These Raman scattering processes are often referred to as "1st order" Raman scattering processes. However, multiple photon excitation—single photon relaxation processes are also observed and are referred to as "hyper Raman scattering" processes. Two photon excitation—one photon relaxation scattering processes are referred to as "2nd order" hyper Raman scattering processes, three-photon excitation—one photon relaxation processes are referred to as "3rd order" Raman scattering processes, etc. These higher order Raman scattering processes are often referred to as "harmonics."

In 2nd order scattering processes, a molecule of the analyte in an initial energy state absorbs the energy from two photons of the incident radiation causing an energy transition in the analyte to a virtual excited state, followed by relaxation to a final energy state and emission of a single scattered photon. If the final energy state is the same as the initial energy state, the scattering process is referred to as hyper Rayleigh scattering. If the final energy state is higher than the initial energy state, the scattering process is referred to as 2nd order Stokes hyper Raman scattering. Finally, if the final energy state is lower than the initial energy state, the scattering process is referred to as 2nd order anti-Stokes hyper Raman scattering. The Stokes and anti-Stokes 2nd order hyper Raman scattering processes are also represented in the Jablonski diagram shown in FIG. 1.

Information may be obtained from hyper Raman scattered radiation that cannot be obtained from 1st order Raman scattered radiation. In particular, vibrational information may be suppressed in Raman scattered radiation due to symmetry issues, thereby resulting in what are often referred to as "silent modes." These silent modes may not be suppressed in the hyper Raman scattered radiation.

When an analyte is irradiated with incident radiation, the scattered radiation may include Raman scattered radiation, which may comprise 1st order Raman scattered radiation (Stokes and anti-Stokes) and higher order hyper Raman scattered radiation (Stokes and anti-Stokes), in addition to Rayleigh scattered radiation. The Raman scattered radiation that is scattered by the analyte (including the hyper Raman scattered radiation) is often referred to as the "Raman signal."

The Raman signal is detected using the radiation detector. The wavelengths and corresponding intensity of the Raman scattered radiation may be determined and used to provide a Raman spectral graph. Analytes generate unique Raman spectral graphs. The unique Raman spectral graph obtained by performing Raman spectroscopy can be used to obtain information relating to the analyte including, but not limited to, the identification of an unknown analyte, or the determination of physical and chemical characteristics of a known analyte.

The number of Raman scattered photons that are scattered by an analyte is extremely small relative to the number of Rayleigh scattered photons, and the number of hyper Raman scattered photons is even smaller than the number of 1st order Raman scattered photons. Typical radiation detectors are capable of detecting the high-intensity Rayleigh scattered radiation in addition to the low-intensity Raman scattered radiation. The detection of the Raman scattered radiation may be difficult due to the high intensity of the Rayleigh scattered radiation. To overcome this difficulty, a radiation filter may be positioned between the analyte stage and the detector to prevent the Rayleigh scattered radiation from being detected by the detector, thus allowing only the Raman scattered radiation to be received by the detector. Commercially available notch filters may be used for such purposes.

After removal of the Rayleigh scattered radiation, the various wavelengths of Raman scattered radiation typically are spatially separated using a diffraction grating. The separated wavelengths of Raman scattered radiation typically are detected or imaged simultaneously using a charge coupled device (CCD) array. Alternatively, the wavelengths of Raman scattered radiation may be detected using a photomultiplier tube (PMT).

Surface-enhanced Raman spectroscopy (SERS) is a technique that allows for enhancement of the intensity of the Raman scattered radiation relative to conventional Raman spectroscopy (i.e., the number of Raman scattered photons that are scattered by an analyte). In SERS, the analyte typically is adsorbed onto or placed adjacent to what is often referred to as a SERS-active structure. SERS-active structures typically include a metal surface or structure. Interactions between the analyte and the metal surface may cause an increase in the intensity of the Raman scattered radiation.

Several types of metallic structures have been employed in SERS techniques to enhance the intensity of Raman scattered radiation that is scattered by an analyte. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface of gold or silver can enhance the Raman scattering intensity by factors of between $10^3$ and $10^6$.

Raman spectroscopy recently has been performed employing metal nanoparticles, such as nanometer scale needles, particles, and wires, as opposed to a simple roughened metallic surface. This process will be referred to herein as nano-enhanced Raman spectroscopy (NERS). Structures comprising nanoparticles that are used to enhance the intensity of Raman scattered radiation may be referred to as NERS-active structures. The intensity of the Raman scattered radiation that is scattered by an analyte adsorbed on such a NERS-active structure can be increased by factors as high as $10^{16}$.

BRIEF SUMMARY OF THE INVENTION

In one aspect, the present invention includes a Raman signal-enhancing structure that includes a first layer of Raman signal-enhancing material, a substantially monomolecular layer of molecules disposed on at least a portion of the first layer of Raman signal-enhancing material, and a second layer of Raman signal-enhancing material disposed on at least a portion of the substantially monomolecular layer of molecules. The second layer of Raman signal-enhancing material is disposed on a side of the layer of molecules opposite the first layer of Raman signal-enhancing material.

In another aspect, the present invention includes a Raman system that includes a radiation source, a Raman signal-enhancing structure, and a radiation detector configured to detect Raman scattered radiation. The Raman signal-enhancing structure includes a first layer of Raman signal-enhancing material, a substantially monomolecular layer of molecules disposed on at least a portion of the first layer of Raman signal-enhancing material, and a second layer of Raman signal-enhancing material disposed on at least a portion of the substantially monomolecular layer of molecules. The second layer of Raman signal-enhancing material is disposed on a side of the layer of molecules opposite the first layer of Raman signal-enhancing material.

In yet an additional aspect, the present invention includes a method of performing Raman spectroscopy. A Raman signal-enhancing structure is provided that includes a first layer of Raman signal-enhancing material, a substantially monomolecular layer of molecules disposed on at least a portion of the first layer of Raman signal-enhancing material, and a second layer of Raman signal-enhancing material disposed on at least a portion of the substantially monomolecular layer of molecules. The second layer of Raman signal-enhancing material is disposed on a side of the layer of molecules opposite the first layer of Raman signal-enhancing material. At least one molecule in the layer of molecules and the Raman signal-enhancing structure are irradiated, and Raman scattered radiation that is scattered by the at least one molecule is detected.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The term "analyte" as used herein means any molecule, molecules, material, substance, or matter that is to be analyzed or detected by Raman spectroscopy.

The term "Raman signal-enhancing material" as used herein means a material that, when formed into appropriate geometries or configurations, is capable of increasing the number of Raman scattered photons that are scattered by an analyte when the analyte is located proximate to that material, and when the analyte and material are subjected to electromagnetic radiation. Raman signal-enhancing materials include, but are not limited to, silver, gold, and copper. Raman signal-enhancing materials generally are capable of exhibiting surface plasmon resonance when they are subjected to electromagnetic radiation at particular wavelengths. Raman signal-enhancing materials are used to form Raman signal-enhancing structures.

The term "Raman signal-enhancing structure" as used herein means a structure that is capable of increasing the number of Raman scattered photons that are scattered by an analyte when the analyte is located proximate to the structure, and the analyte and structure are subjected to electromagnetic radiation. Raman signal-enhancing structures include SERS-active structures and NERS-active structures.

The term "monomolecular layer of molecules" as used herein means a layer of molecules occupying an area on a surface that is substantially equal to the effective cross-sectional area of one molecule multiplied by the number of molecules in the layer of molecules.

The term "substantially monomolecular layer of molecules" as used herein means a layer of molecules occupying an area on a surface that is between about 80 percent and about 110 percent of an area equal to the effective cross-sectional area of one molecule multiplied by the number of molecules in the layer of molecules.

The illustrations presented herein are not meant to be actual views of any particular Ramen-enhancing structure or Raman spectroscopy system, but are merely idealized representations which are employed to describe the present invention. Additionally, elements common between figures may retain the same numerical designation.

Figure 2:
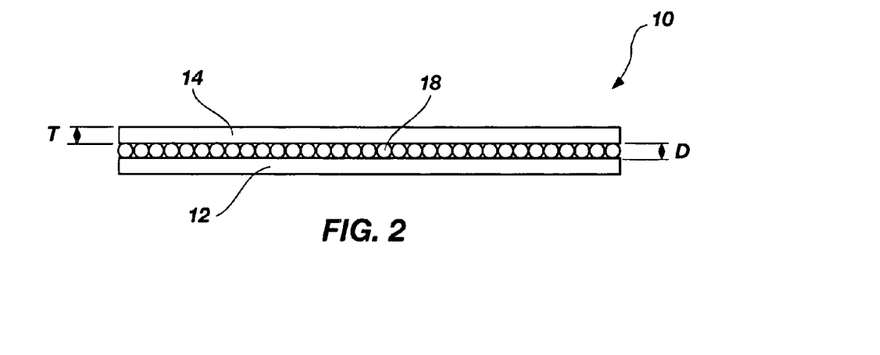
FIG. 2 is a side view of a particular embodiment of a Raman signal-enhancing structure of the present invention.

A Raman signal-enhancing structure 10 that embodies teachings of the present invention is shown in FIG. 2. The Raman signal-enhancing structure 10 includes a first layer of Raman signal-enhancing material 12, a plurality of molecules 18 disposed on at least a portion of the first layer of Raman signal-enhancing material 12, and a second layer of Raman signal-enhancing material 14 disposed on at least a portion of the plurality of molecules 18. Each of the first layer of Raman signal-enhancing material 12 and the second layer of Raman signal-enhancing material 14 may be substantially planar.

Furthermore, the plurality of molecules 18 may be disposed in a substantially monomolecular layer of molecules 18.

At least one of the first layer of Raman signal-enhancing material 12 and the second layer of Raman signal-enhancing material 14 may be sufficiently thin to be transparent to electromagnetic radiation having wavelengths in a range in which it is desired to conduct Raman spectroscopy. For example, at least one of the first layer of Raman signal-enhancing material 12 and the second layer of Raman signal-enhancing material 14 may be sufficiently thin to be transparent to electromagnetic radiation having wavelengths in a range from about 100 nanometers to about 5000 nanometers. In one embodiment, at least one of the first layer of Raman signal-enhancing material 12 and the second layer of Raman signal-enhancing material 14 may have a thickness T that is less than about ten nanometers.

Each molecule 18 of the plurality of molecules 18 may be identical. Furthermore, the plurality of molecules 18 may form a monomolecular layer of molecules 18. In this configuration, the distance D separating the second layer of Raman signal-enhancing material 14 from the first layer of Raman signal-enhancing material 12 may be substantially uniform across the Raman signal-enhancing structure 10. Furthermore, the thickness of the monomolecular layer of molecules 18, and thus the distance D, may be less than about five nanometers. Moreover, each molecule 18 of the plurality of molecules 18 may be an analyte on which it is desired to conduct Raman spectroscopy.

Figure 3A:
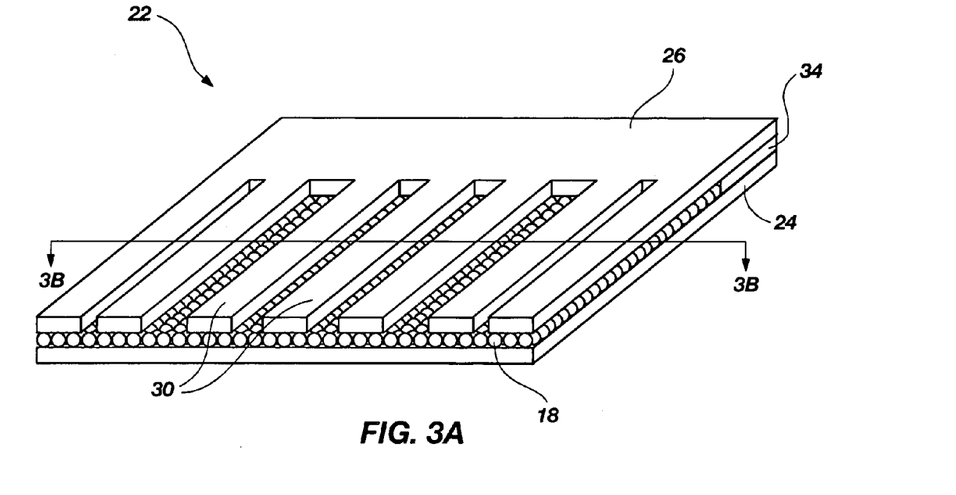
FIG. 3A is a perspective view of a particular embodiment of another Raman signal-enhancing structure of the present invention.
Figure 3B:
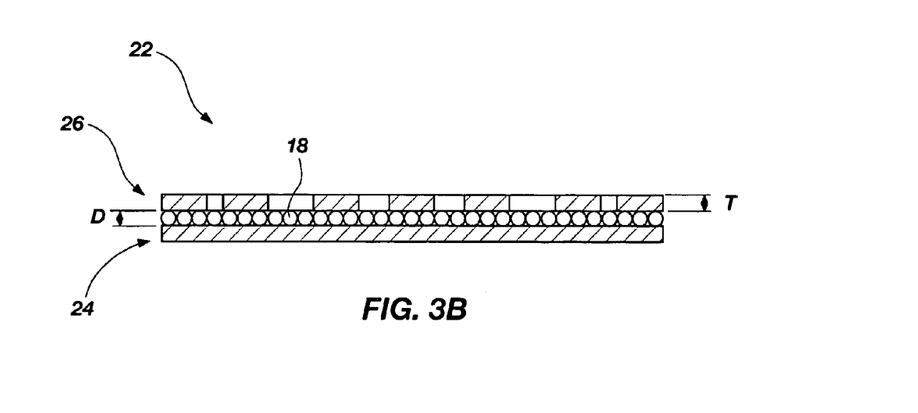
FIG. 3B is a cross-sectional view of the Raman signal-enhancing structure shown in FIG. 3A taken along section line 3B-3B shown therein.

Another Raman signal-enhancing structure 22 that embodies teachings of the present invention is shown in FIGS. 3A-3B. Similar to the previously described Raman signal-enhancing structure 22, the Raman signal-enhancing structure 22 also includes a first layer of Raman signal-enhancing material 24, a plurality of molecules 18 disposed on at least a portion of the first layer of Raman signal-enhancing material 24, and a second layer of Raman signal-enhancing material 26 disposed on at least a portion of the plurality of molecules 18. Each of the first layer of Raman signal-enhancing material 24 and the second layer of Raman signal-enhancing material 26 may be substantially planar. Furthermore, the plurality of molecules 18 may be disposed in a substantially monomolecular layer of molecules 18. Each molecule 18 of the plurality of molecules 18 may be an analyte on which it is desired to conduct Raman spectroscopy.

As shown in FIG. 3A, the second layer of Raman signal-enhancing material 26 may be discontinuous. By way of example and not limitation, at least a portion of the second layer of Raman signal-enhancing material 26 may include a plurality of elongated members 30 separated from one another by elongated voids or channels that extend through the second layer of Raman signal-enhancing material 26.

A support structure 34 may be disposed between a portion of the first layer of Raman signal-enhancing material 24 and a portion of the second layer of Raman signal-enhancing material 26. The support structure 34 may be formed from virtually any type of material including, for example, metal materials, ceramic materials, semiconductor type materials, or polymer materials. By way of example and not limitation, the support structure 34 may be formed from the same material used to form the first layer of Raman signal-enhancing material 26. The support structure 34 may be secured or adhered to both first layer of Raman signal-enhancing material 24 and the second layer of Raman signal-enhancing material 26, and may prevent movement of the first layer of Raman signal-enhancing material 24 relative to the second layer of Raman signal-enhancing material 26. In this manner, the support structure 34 may provide additional structural support and rigidity to the Raman signal-enhancing structure 22.

Referring to FIG. 3B, the size and shape of each molecule 18, in addition to the orientation of the molecules 18, may define the distance D between the first layer of Raman signal-enhancing material 24 and the second layer of Raman signal-enhancing material 26.

At least one of the first layer of Raman signal-enhancing material 24 and the second layer of Raman signal-enhancing material 26 may be sufficiently thin to be transparent to electromagnetic radiation having wavelengths in a range from about 100 nanometers to about 5000 nanometers. In one embodiment, at least one of the first layer of Raman signal-enhancing material 24 and the second layer of Raman signal-enhancing material 26 may have a thickness T that is less than about ten nanometers.

Each elongated member 30 may have a selected, predetermined size and shape. By way of example and not limitation, each elongated member 30 may have a shape that is substantially rectangular, as shown in FIG. 3A, and may have a selected, predetermined length and width. The length and width of each elongated member 30 may be the same as or different from the length and width of other elongated members 30. Furthermore, the spacing or distance between adjacent elongated members 30 may be varied in order to provide a number of different spacings in the Raman signal-enhancing structure 22. The length and width of the elongated members 30, in addition to the spacing between adjacent elongated members 30, may be selected to optimize the Raman signal emitted by the molecules 18 or any other analyte that is disposed proximate the elongated members 30 and irradiated by incident electromagnetic radiation.

In alternative embodiments in which the second layer of Raman signal-enhancing material 26 is discontinuous, the second layer of Raman signal-enhancing material 26 may include a plurality of apertures extending through the second layer of Raman signal-enhancing material 26. The apertures may have a cross-sectional shape that is substantially circular, square, or any other shape. Furthermore, the apertures could be selectively located in an ordered array in the second layer of Raman signal-enhancing material 26, or the apertures could be randomly located in the second layer of Raman signal-enhancing material 26.

In the embodiment shown in FIGS. 3A and 3B, the first layer of Raman signal-enhancing material 24 is substantially continuous. In alternative embodiments, the first layer of Raman signal-enhancing material 24 may be discontinuous and may have any of the configurations previously described in relation to the second layer of Raman signal-enhancing material 26.

Figure 4:
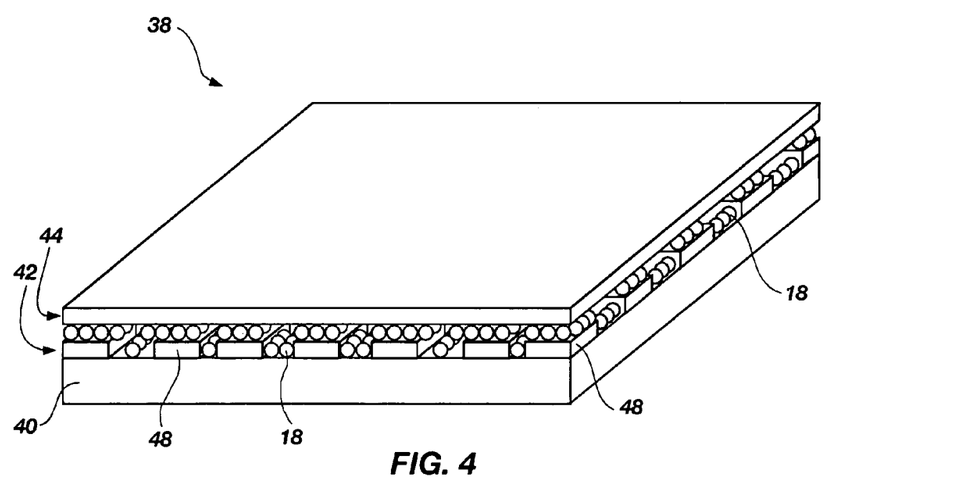
FIG. 4 is a perspective view of a particular embodiment of another Raman signal-enhancing structure of the present invention.

Another Raman signal-enhancing structure 38 that embodies teachings of the present invention is shown in FIG. 4. Similar to the previously described Raman signal-enhancing structures, the Raman signal-enhancing structure 38 also includes a first layer of Raman signal-enhancing material 42, a plurality of molecules 18 disposed on at least a portion of the first layer of Raman signal-enhancing material 42, and a second layer of Raman signal-enhancing material 44 disposed on at least a portion of the plurality of molecules 18. Each of the first layer of Raman signal-enhancing material 42 and the second layer of Raman signal-enhancing material 44 may be substantially planar. Furthermore, the plurality of molecules 18 may be disposed in a substantially monomolecular layer of molecules 18. Each molecule 18 of the plurality of molecules 18 may be an analyte on which it is desired to conduct Raman spectroscopy.

At least one of the first layer of Raman signal-enhancing material 42 and the second layer of Raman signal-enhancing material 44 may be sufficiently thin to be transparent to electromagnetic radiation having wavelengths in a range in which it is desired to conduct Raman spectroscopy.

In contrast to the previously described Raman signal-enhancing structures, the Raman signal-enhancing structure 38 shown in FIG. 4 further includes a substrate 40.

As illustrated in FIG. 4, the first layer of Raman signal-enhancing material 42 may be discontinuous and the second layer of Raman signal-enhancing material 44 may be substantially continuous. By way of example and not limitation, at least a portion of the first layer of Raman signal-enhancing material 42 may include a plurality of isolated islands 48 separated from one another by voids or channels that extend through the first layer of Raman signal-enhancing material 42. Each isolated island 48 may have a selected, predetermined size and shape. For example, the isolated islands 48 may have a cross-sectional shape that is substantially square. Alternatively, the isolated islands 48 may have a cross-sectional shape that is substantially circular, rectangular, triangular, or any other shape.

Although the second layer of Raman signal-enhancing material 44 appears substantially planar in FIG. 4, the second layer of Raman signal-enhancing material 44 may at least partially conform to the underlying topography of the first layer of Raman signal-enhancing material 42 and the layer of molecules 18, and may not be substantially planar. Furthermore, the Raman signal-enhancing structure 38 may include a support structure (not shown) substantially identical to the support structure 34 previously described herein in relation to the Raman signal-enhancing structure 22 shown in FIG. 3A.

Figure 5A:
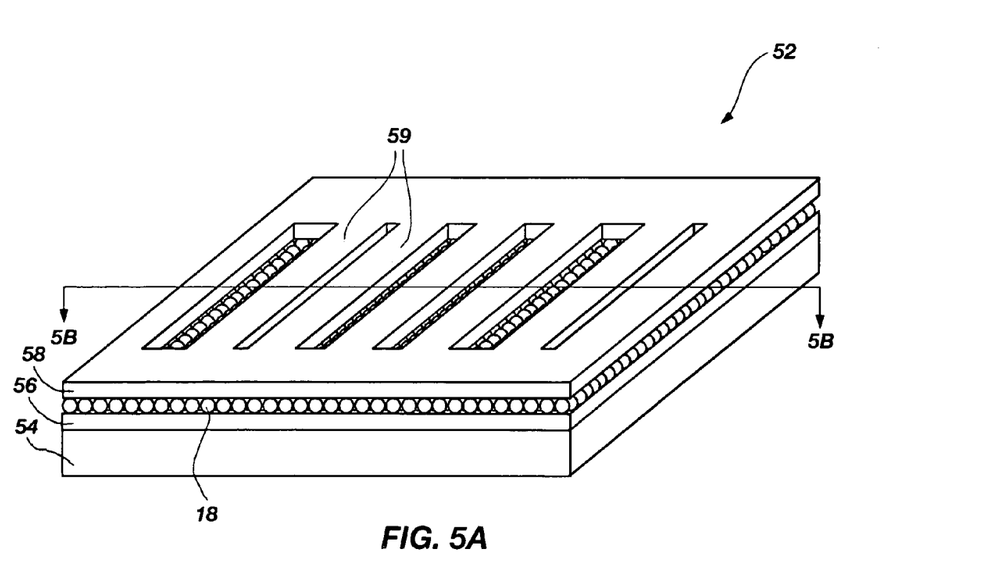
FIG. 5A is a perspective view of a particular embodiment of another Raman signal-enhancing structure of the present invention.
Figure 5B:
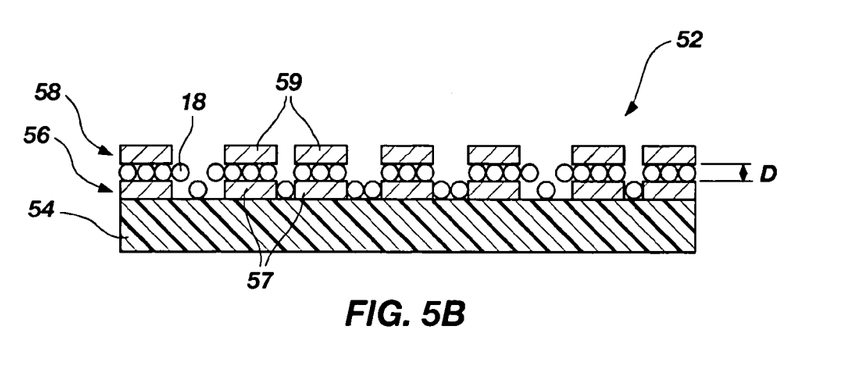
FIG. 5B is a cross-sectional view of the Raman signal-enhancing structure shown in FIG. 5A taken along section line 5B-5B shown therein.

Another Raman signal-enhancing structure 52 that embodies teachings of the present invention is shown in FIGS. 5A-5B. The Raman signal-enhancing structure 52 may include a substrate 54, a first layer of Raman signal-enhancing material 56, a plurality of molecules 18 disposed on at least a portion of the first layer of Raman signal-enhancing material 56, and a second layer of Raman signal-enhancing material 58 disposed on at least a portion of the plurality of molecules 18. Each of the first layer of Raman signal-enhancing material 56 and the second layer of Raman signal-enhancing material 58 may be substantially planar. Furthermore, the plurality of molecules 18 may be disposed in a substantially monomolecular layer of molecules 18. Each molecule 18 of the plurality of molecules 18 may be an analyte on which it is desired to conduct Raman spectroscopy.

The second layer of Raman signal-enhancing material 58 may be sufficiently thin to be transparent to electromagnetic radiation having wavelengths in a range in which it is desired to conduct Raman spectroscopy. As previously discussed, the size and shape of each molecule 18, in addition to the orientation of the molecules 18, may define the distance D (FIG. 5B) between the first layer of Raman signal-enhancing material 56 and the second layer of Raman signal-enhancing material 58.

The first layer of Raman signal-enhancing material 56 and the second layer of Raman signal-enhancing material 58 each may be discontinuous. As seen in FIG. 5A, a plurality of elongated substantially rectangular apertures may be formed through at least a portion of the second layer of Raman signal-enhancing material 58. The elongated apertures may define a plurality of elongated members 59 separated from one another by the elongated apertures that extend through the second layer of Raman signal-enhancing material 58. Each elongated aperture and, thus, each elongated member 59, may have a selected length and width. Furthermore, the selected length and width of each elongated member 59 may be equal to or different from the selected length and width of other elongated members 59 of the Raman signal-enhancing structure 52.

Referring to FIG. 5B, a plurality of elongated, substantially rectangular apertures may be formed through at least a portion of the first layer of Raman signal-enhancing material 56. The elongated apertures may define a plurality of elongated members 57 separated from one another by the elongated apertures that extend through the first layer of Raman signal-enhancing material 56. Each elongated aperture, and thus each elongated member 57, may have a selected length and width. Furthermore, the selected length and width of each elongated member 57 may be equal to or different from the selected length and width of other elongated members 57 of the Raman signal-enhancing structure 52. In this configuration, the first layer of Raman signal-enhancing material 56 and the second layer of Raman signal-enhancing material 58 may be substantially identical and aligned with one another such that the elongated members 57 of the first layer of Raman signal-enhancing material 56 are substantially aligned with the elongated members 59 of the second layer of Raman signal-enhancing material 58, as shown in FIG. 5B.

The distance D separating the second layer of Raman signal-enhancing material 58 from the first layer of Raman signal-enhancing material 56 and the length and width of the elongated members 57 and the elongated members 59 may be designed and selected to optimize a Raman signal emitted by at least one molecule 18 or other analyte upon which Raman spectroscopy is to be performed using the Raman signal-enhancing structure 52.

In alternative embodiments, the second layer of Raman signal-enhancing material 58 may be selectively located or positioned relative to the first layer of Raman signal-enhancing material 56 such that the elongated members 59 of the second layer of Raman signal-enhancing material 58 are offset by a selected distance relative to the elongated members 57 of the first layer of Raman signal-enhancing material 56. Moreover, the first layer of Raman signal-enhancing material 56 and the second layer of Raman signal-enhancing material 58 may not be substantially identical.

Figure 6A:
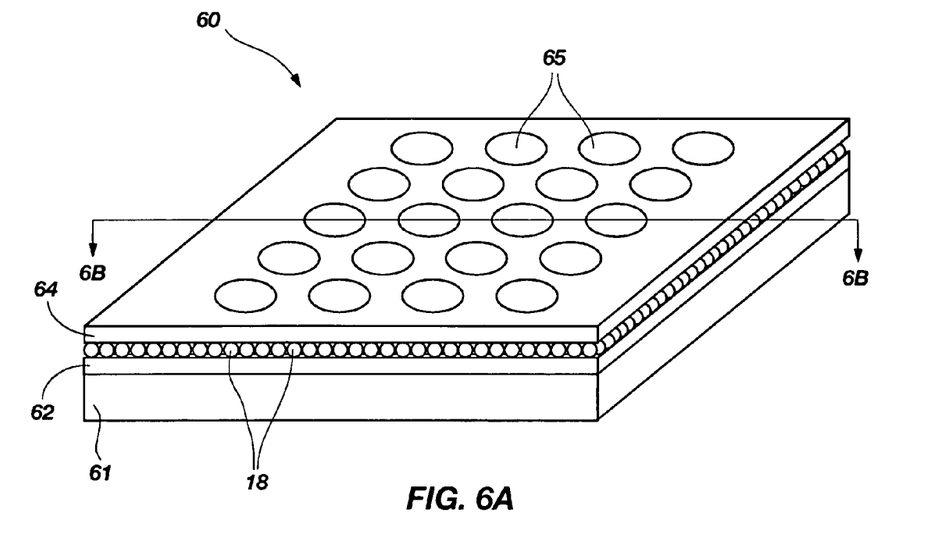
FIG. 6A is a perspective view of a particular embodiment of another Raman signal-enhancing structure of the present invention.
Figure 6B:
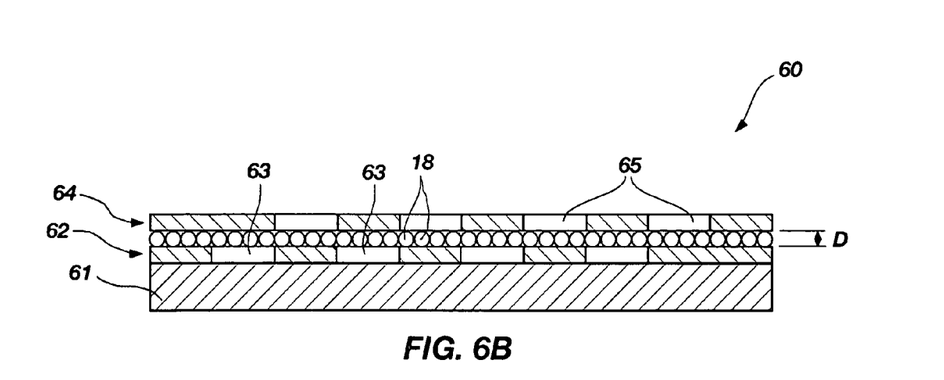
FIG. 6B is a cross-sectional view of the Raman signal-enhancing structure shown in FIG. 6A taken along section line 6B-6B shown therein.

Another Raman signal-enhancing structure 60 that embodies teachings of the present invention is shown in FIGS. 6A-6B. The Raman signal-enhancing structure 60 may include a substrate 61, a first layer of Raman signal-enhancing material 62, a plurality of molecules 18 disposed on at least a portion of the first layer of Raman signal-enhancing material 62, and a second layer of Raman signal-enhancing material 64 disposed on at least a portion of the plurality of molecules 18. Each of the first layer of Raman signal-enhancing material 62 and the second layer of Raman signal-enhancing material 64 may be substantially planar. Furthermore, the plurality of molecules 18 may be disposed in a substantially monomolecular layer of molecules 18. Each molecule 18 of the plurality of molecules 18 may be an analyte on which it is desired to conduct Raman spectroscopy.

The second layer of Raman signal-enhancing material 64 may be sufficiently thin to be transparent to electromagnetic radiation having wavelengths in a range in which it is desired to conduct Raman spectroscopy. As previously discussed, the size and shape of each molecule 18, in addition to the orientation of the molecules 18, may define the distance D (FIG. 6B) between the first layer of Raman signal-enhancing material 62 and the second layer of Raman signal-enhancing material 64.

The first layer of Raman signal-enhancing material 62 and the second layer of Raman signal-enhancing material 64 each may be discontinuous. As seen in FIG. 6A, a plurality of substantially cylindrical apertures 65 may be formed through the second layer of Raman signal-enhancing material 64. Each aperture 65 may have a selected, predefined diameter. Furthermore, the selected, predefined diameter of each aperture 65 may be equal to or different from the selected, predefined diameter of other apertures 65 in the second layer of Raman signal-enhancing material 64.

Referring to FIG. 6B, a plurality of substantially cylindrical apertures 63 may be formed through the first layer of Raman signal-enhancing material 62. Each aperture 63 may have a selected, predefined diameter. Furthermore, the selected, predefined diameter of each aperture 63 may be equal to or different from the selected, predefined diameter of other apertures 63 in the first layer of Raman signal-enhancing material 62. In this configuration, the first layer of Raman signal-enhancing material 62 and the second layer of Raman signal-enhancing material 64 may be substantially identical and aligned with one another such that the apertures 63 in the first layer of Raman signal-enhancing material 62 are offset or staggered with respect to the apertures 65 in the second layer of Raman signal-enhancing material 64, as shown in FIG. 6B.

The distance D separating the second layer of Raman signal-enhancing material 64 from the first layer of Raman signal-enhancing material 62 and the selected, predetermined diameter of each aperture 63 and each aperture 65 may be designed and selected to optimize a Raman signal emitted by at least one molecule 18 or other analyte upon which Raman spectroscopy is to be performed using the Raman signal-enhancing structure 60.

Figure 7:
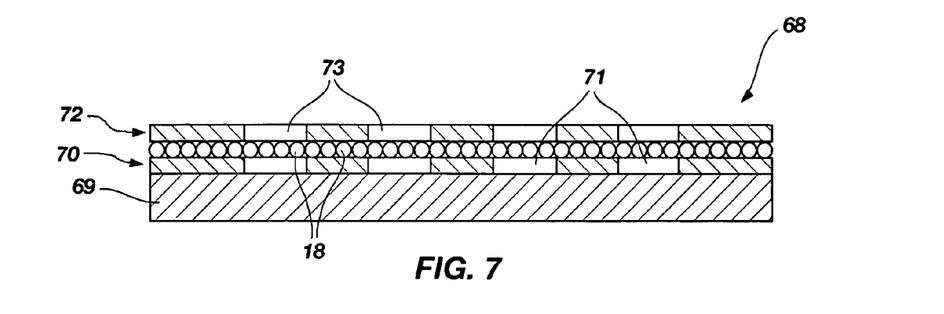
FIG. 7 is a cross-sectional side view of a particular embodiment of another Raman signal-enhancing structure of the present invention.

Another Raman signal-enhancing structure 68 that embodies teachings of the present invention is shown in FIG. 7. The Raman signal-enhancing structure 68 is substantially similar to the Raman signal-enhancing structure 60 shown in FIGS. 6A-6B and includes a substrate 69, a first layer of Raman signal-enhancing material 70, a plurality of molecules 18 disposed on at least a portion of the first layer of Raman signal-enhancing material 70, and a second layer of Raman signal-enhancing material 72 disposed on at least a portion of the plurality of molecules 18. Each of the first layer of Raman signal-enhancing material 70 and the second layer of Raman signal-enhancing material 72 may be substantially planar. Furthermore, the plurality of molecules 18 may be disposed in a substantially monomolecular layer of molecules 18. Each molecule 18 of the plurality of molecules 18 may be an analyte on which it is desired to conduct Raman spectroscopy.

A plurality of apertures 71 may be formed through the first layer of Raman signal-enhancing material 70, and a plurality of apertures 73 may be formed through the second layer of Raman signal-enhancing material 72. Each aperture 71 and each aperture 73 may be substantially cylindrical and may have a selected, predefined diameter. The first layer of Raman signal-enhancing material 70 and the second layer of Raman signal-enhancing material 72 may be substantially identical and aligned with one another such that the apertures 71 in the first layer of Raman signal-enhancing material 70 are substantially aligned with the apertures 73 in the second layer of Raman signal-enhancing material 72, as shown in FIG. 7.

Figure 8:
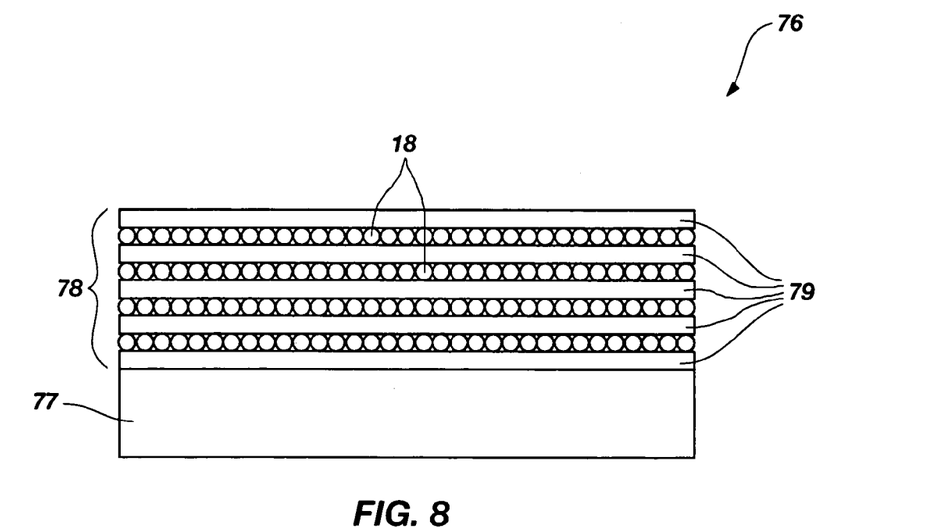
FIG. 8 is a side view of another particular embodiment of the Raman signal-enhancing structure of the present invention.

Another Raman signal-enhancing structure 76 that embodies teachings of the present invention is shown in FIG. 8. The Raman signal-enhancing structure 76 includes multilayer stack 78 comprising a plurality of substantially planar layers of Raman signal-enhancing material 79. Each layer of Raman signal-enhancing material 79 is separated from adjacent layers of Raman signal-enhancing material 79 by a substantially monomolecular layer of molecules 18. The thickness of each monomolecular layer of molecules 18 may define the distance separating the adjacent layers of Raman signal-enhancing material 79. Moreover, each molecule 18 of the plurality of molecules 18 may be identical, and may be an analyte on which it is desired to conduct Raman spectroscopy. The Raman signal-enhancing structure 76 may further include a substrate 77.

Each layer of Raman signal-enhancing material 79 may be sufficiently thin to be transparent to electromagnetic radiation having wavelengths in a range in which it is desired to conduct Raman spectroscopy. Furthermore, each layer of Raman signal-enhancing material 79 may be substantially continuous and substantially planar.

In alternative embodiments, one or more layers of Raman signal-enhancing material 79 may be discontinuous. By way of example and not limitation, one or more layers of Raman signal-enhancing material 79 may have a configuration substantially identical to that of the second layer of Raman signal-enhancing material 26 of the Raman signal-enhancing structure 22 shown in FIG. 3A, the first layer of Raman signal-enhancing material 42 of the Raman signal-enhancing structure 38 shown in FIG. 4, the second layer of Raman signal-enhancing material 58 of the Raman signal-enhancing structure 52 shown in FIG. 5A, or the second layer of Raman signal-enhancing material 64 of the Raman signal-enhancing structure 60 shown in FIG. 6A. In addition, one or more of the layers of Raman signal-enhancing material 79 shown in FIG. 8 may not be substantially planar.

Each of the Raman signal-enhancing structures previously described herein includes a generally layered structure, which may be fabricated in a layer-by-layer sequence. Each of the previously described Raman signal-enhancing structures may be fabricated using substantially similar methods. Methods for forming the Raman signal-enhancing structure 60 shown in FIGS. 6A-6B are described below. The methods described below in relation to the Raman signal-enhancing structure 60 may be used, and slightly adapted if necessary, to form any of the previously described Raman signal-enhancing structures.

Referring to FIG. 6A, a substrate 61 may be provided. The substrate may include a relatively thick, planar layer of metal material, ceramic material, or polymer material. For example, the substrate may be a commercially available silica or sapphire substrate having a thickness on the order of tens to hundreds of millimeters. Such substrates are commercially available.

A substantially planar and continuous layer of Raman signal-enhancing material may be deposited over the substrate 61 using physical vapor deposition techniques (PVD) including, but not limited to thermal evaporation techniques, electron-beam evaporation techniques, filament evaporation techniques, and sputtering techniques. Alternatively, the substantially planar and continuous layer of Raman signal-enhancing material may be deposited over the substrate 61 using electrodeposition techniques or chemical vapor deposition techniques (CVD) including, but not limited to, atomic layer deposition techniques.

After forming a substantially planar and continuous layer of Raman signal-enhancing material, the apertures 63 (FIG. 6B) may be formed in the layer of Raman signal-enhancing material to form the first layer of Raman signal-enhancing material 62 shown in FIGS. 6A-6B. The apertures 63 may be formed using various methods including, for example, photolithography, electron beam lithography, or focused ion beam lithography. By way of example and not limitation, the apertures 63 may be formed in the continuous layer of Raman signal-enhancing material by applying a photoresist material to a surface of the layer of Raman signal-enhancing material, patterning the photoresist material using a mask, and etching the apertures in surfaces of the layer of Raman signal-enhancing material that are exposed through the photoresist material. Etching techniques may include, for example, chemical etching or reactive ion etching.

After forming the first layer of Raman signal-enhancing material 62, a substantially monomolecular layer of molecules 18 may be deposited over at least a portion of the first layer of Raman signal-enhancing material 62. The substantially monomolecular layer of molecules 18 may be deposited using Langmuir film and Langmuir-Blodgett film techniques. These techniques generally include forming a substantially monomolecular layer of molecules 18 on a surface of a liquid and passing the substrate 61 and the first layer of Raman signal-enhancing material 62 through the substantially monomolecular layer of molecules 18 to transfer the substantially monomolecular layer of molecules 18 to the surface of the first layer of Raman signal-enhancing material 62. Equipment for depositing Langmuir films and Langmuir-Blodgett films is commercially available from, for example, KSV Instruments of Helsinki, Finland.

In alternative methods, a plurality of molecules 18 may be suspended in a liquid, and the suspension may be applied to a surface of the first layer of Raman signal-enhancing material 62. The liquid then may be allowed to evaporate, leaving the molecules 18 on the surface of the first layer of Raman signal-enhancing material 62. In yet other methods, the substantially monomolecular layer of molecules 18 may be formed by simply adsorbing the molecules 18 on the surface of the first layer of Raman signal-enhancing material.

Additionally, the molecules 18 may be bound to a surface of the first layer of Raman signal-enhancing material 62 using an intermediate binding molecule or material (not shown). The binding material may include any molecule or material that will bind to the molecules 18. By way of example and not limitation, the binding material may include molecules that, together with the molecules 18, form what is known in the art as a "specific pair" or a "recognition pair" of molecules. For example, if the molecules 18 are an antigen or an antibody, the binding material may include a complementary antigen or antibody. Many biomolecules act as receptors or ligands to other biomolecules. If the molecules 18 are or include such biomolecules, the binding material may include a complementary biomolecule.

If the Raman signal-enhancing structure 60 is to include a support structure such as, for example, the support structure 34 shown in FIG. 3A, the support structure may be formed using techniques substantially similar to the previously described methods for forming the first layer of Raman signal-enhancing material. By way of example and not limitation, a support structure 34 may be formed on a portion of the first layer of Raman signal-enhancing material 62 using physical vapor deposition (PVD) techniques or chemical vapor deposition techniques (CVD). If the support structure 34 includes a curable polymer material, the polymer material may be spun over the first layer of Raman signal-enhancing material 62 in the liquid state and subsequently cured to the solid state. If necessary, the support structure 34 may be formed by first depositing a layer of material and subsequently removing portions or regions of the material using, for example, electron beam lithography, focused ion beam lithography, or photolithography.

After a substantially monomolecular layer of molecules 18 has been deposited over at least a portion of the first layer of Raman signal-enhancing material 62, another layer of Raman signal-enhancing material may be deposited over at least a portion of the substantially monomolecular layer of molecules 18. By way of example and not limitation, the layer of Raman signal-enhancing material may be deposited over the layer of molecules 18 using physical vapor deposition techniques (PVD) including, but not limited to, thermal evaporation techniques, electron-beam evaporation techniques, filament evaporation techniques, and sputtering techniques.

After depositing another layer of Raman signal-enhancing material over the layer of molecules 18, the apertures 65 may be formed in the layer of Raman signal-enhancing material to form the first layer of Raman signal-enhancing material 64 shown in FIGS. 6A-6B. The apertures 65 may be formed using various methods including, for example, photolithography, electron beam lithography, or focused ion beam lithography. By way of example and not limitation, the apertures 65 may be formed in the continuous layer of Raman signal-enhancing material by applying a photoresist material to a surface of the layer of Raman signal-enhancing material, patterning the photoresist material using a mask, and etching the apertures in surfaces of the layer of Raman signal-enhancing material that are exposed through the photoresist material. Etching techniques may include, for example, chemical etching or reactive ion etching.

The methods described in the preceding paragraphs allow for relatively simple methods for precisely fabricating Raman signal-enhancing structures that include analyte molecules disposed in nanometer sized gaps between adjacent structures that are formed from or include a Raman signal-enhancing material.

Raman signal-enhancing structures that embody teachings of the present invention may be used in Raman spectroscopy systems to perform Raman spectroscopy on an analyte.

Figure 9:
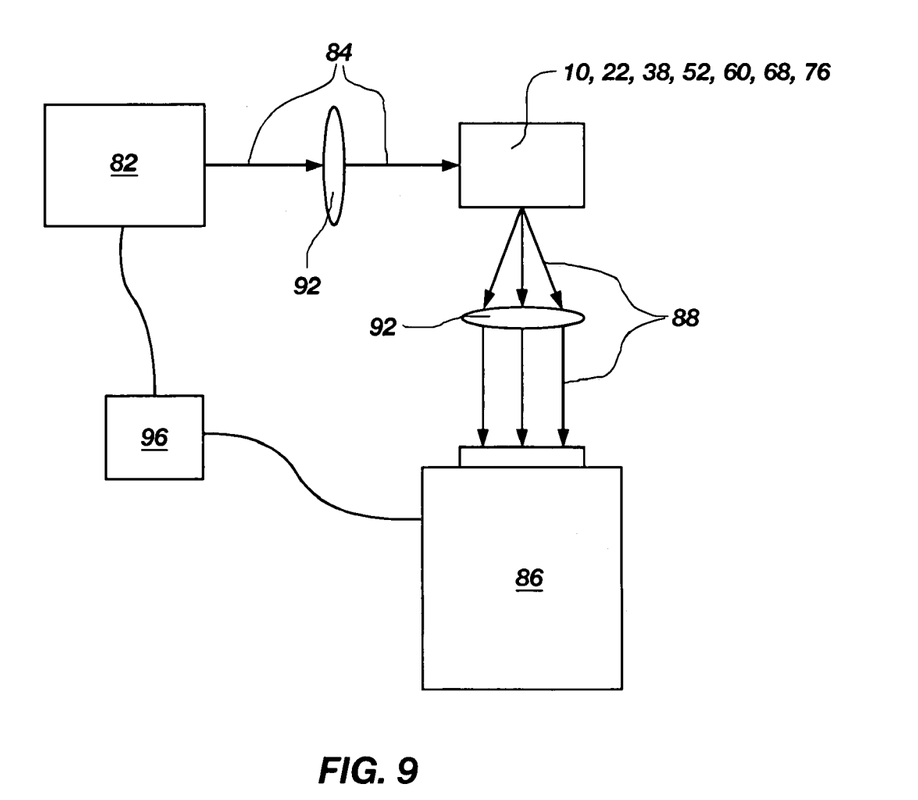
FIG. 9 is a schematic diagram of a particular embodiment of a Raman system of the present invention.

FIG. 9 is a schematic diagram of an exemplary Raman spectroscopy system 80 that embodies teachings of the present invention. The Raman spectroscopy system 80 includes an electromagnetic radiation source 82 that is configured to provide incident radiation 84, an electromagnetic radiation detector 86 that is configured to detect Raman scattered radiation 88 that is scattered by an analyte, and a Raman signal-enhancing structure that embodies teachings of the present invention, such as, for example, any one of the previously described Raman signal-enhancing structures 10, 22, 38, 52, 60, 68, and 64. The Raman spectroscopy system 80 also may include various optical components 92 (such as, for example, apertures, lenses, and filters) positioned between the electromagnetic radiation source 82 and the Raman signal-enhancing structure 10, 22, 38, 52, 60, 68, 64, and between the Raman signal-enhancing structure and the radiation detector 86.

The radiation source 82 may include any suitable source for emitting incident electromagnetic radiation 84 at a desired wavelength and may be capable of emitting a tunable wavelength of monochromatic incident electromagnetic radiation 84. For example, commercially available semiconductor lasers, helium-neon lasers, carbon dioxide lasers, radiation emitting diodes, incandescent lamps, vertical cavity surface emitting lasers, edge emitting lasers, and many other known radiation emitting sources can be used as the electromagnetic radiation source 82. If necessary, a radiation filter may be used in conjunction with the electromagnetic radiation source 82 to provide monochromatic incident electromagnetic radiation 84. The wavelengths that are emitted by the electromagnetic radiation source 82 may be any suitable wavelength for performing Raman spectroscopy on the analyte, and may be within or near the visible region of the electromagnetic radiation spectrum.

The radiation detector 86 receives and detects the Raman scattered radiation 88 that includes Raman scattered photons that are scattered by an analyte located proximate the Raman signal-enhancing structure 10, 22, 38, 52, 60, 68, 64. The radiation detector 86 may include a device for determining the wavelength of the Raman scattered radiation 88 and a device for determining the intensity of the Raman scattered radiation 88. By way of example and not limitation, the radiation detector 86 may include a monochromator and a photomultiplier tube. As another example, the radiation detector 86 may include a wavelength dispersive grating and a charge coupled device. Typically, the Raman scattered radiation 88 is scattered in all directions relative to the Raman signal-enhancing structure.

Optical components 92 positioned between the electromagnetic radiation source 82 and the Raman signal-enhancing structure 10, 22, 38, 52, 60, 68, 64 can be used to collimate, filter, or focus the incident electromagnetic radiation 84 before the incident electromagnetic radiation 84 impinges on the Raman signal-enhancing structure and the analyte. Optical components 92 positioned between the Raman signal-enhancing structure 10, 22, 38, 52, 60, 68, 64 and the radiation detector 86 can be used to collimate, filter, or focus the Raman scattered radiation 88.

Raman spectroscopy system 80 also may include a system controller 96 for controlling the radiation source 82, the radiation detector 86. The system controller 96 may include an input system for allowing a user to control the operation of the components of the Raman spectroscopy system 80, and an output system for displaying or otherwise conveying information obtained from the Raman scattered radiation 88. The system controller 96 may further include a computer device including a signal processor and memory for collecting, storing, and otherwise manipulating data relating to the Raman signal obtained from the radiation detector 86.

It should be understood that Raman spectroscopy systems that embody teachings of the present invention may be provided in many forms, such as, for example, conventional table top systems or small portable Raman spectroscopy systems. For example, an exemplary Raman spectroscopy system that embodies teachings of the present invention may include a probe comprising one of the previously described Raman signal-enhancing structures 10, 22, 38, 52, 60, 68, 64. Fiber optic cables or wires may be used to transport the incident electromagnetic radiation 84 from the radiation source 82 to the probe and to deliver Raman scattered radiation 88 from the probe to the radiation detector 86. The radiation source 82, the radiation detector 86, and the system controller 96 may be provided in a single portable unit to provide a relatively small, portable Raman spectroscopy system.

Figure 10:
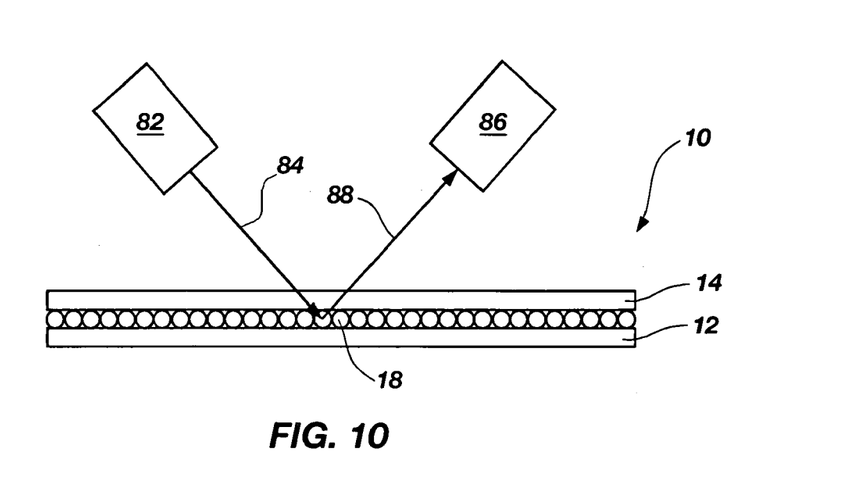
FIG. 10 is a schematic diagram of another Raman system of the present invention that includes the Raman signal-enhancing structure shown in FIG. 2.

The Raman signal-enhancing structure 10, previously described in relation to FIG. 2, is shown in FIG. 10 being irradiated with incident electromagnetic radiation 84 emitted by the radiation source 82. As seen therein, the radiation source 82 may be oriented relative to the Raman signal-enhancing structure 10 such that the incident radiation 84 impinges on the Raman signal-enhancing structure 10 at an angle. As the second layer of Raman signal-enhancing material 14 is at least partially transparent to the incident electromagnetic radiation 84, at least some of the incident electromagnetic radiation 84 may pass through the second layer of Raman signal-enhancing material 14 and impinge on at least one molecule 18. The at least one molecule 18 may inelastically scatter at least some of the incident electromagnetic radiation 84, thereby generating Raman scattered radiation 88. In one embodiment, the radiation detector 86 may be oriented relative to the radiation source 82 such that the radiation detector collects and receives Raman scattered radiation 88 that is scattered at a substantially right angle relative to the incident electromagnetic radiation 84. The Raman scattered radiation 88 then can be analyzed to identify or characterize the at least one molecule 18.

Figure 11:
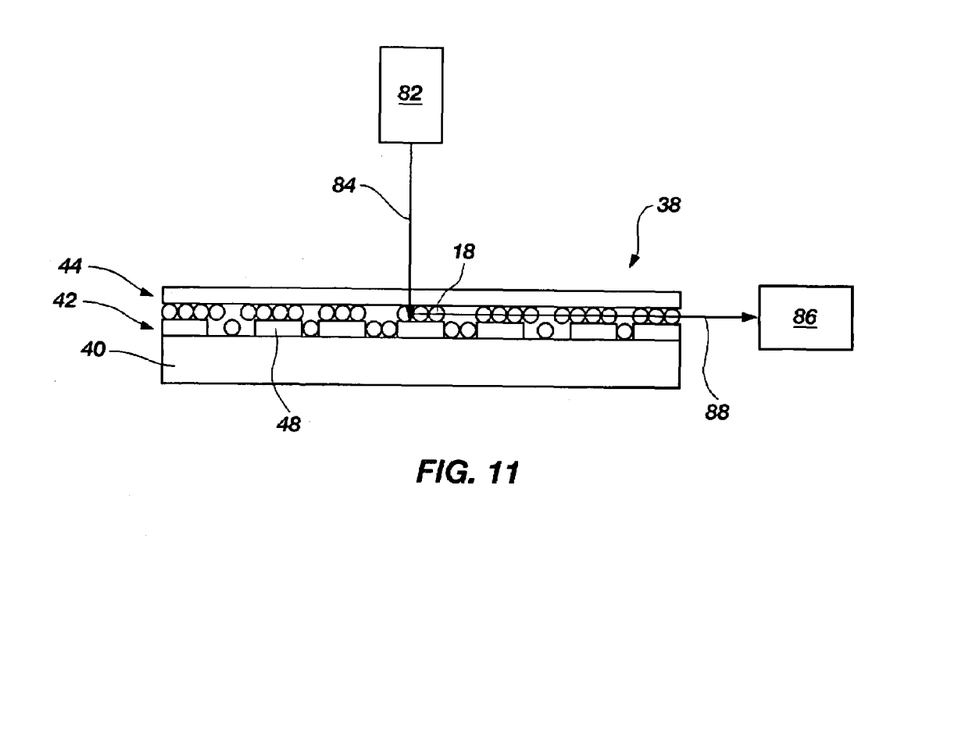
FIG. 11 is a schematic diagram of another Raman system of the present invention that includes the Raman signal-enhancing structure shown in FIG. 4.

The Raman signal-enhancing structure 38, previously described in relation to FIG. 4, is shown in FIG. 11 being irradiated with incident electromagnetic radiation 84 emitted by the radiation source 82. As seen therein, the radiation source 82 may be oriented relative to the Raman signal-enhancing structure 38 such that the incident radiation 84 impinges on the Raman signal-enhancing structure 38 in a direction substantially normal to the substantially planar second layer of Raman signal-enhancing material 44. As the second layer of Raman signal-enhancing material 44 is at least partially transparent to the incident electromagnetic radiation 84, at least some of the incident electromagnetic radiation 84 may pass through the second layer of Raman signal-enhancing material 44 and impinge on at least one molecule 18. The at least one molecule 18 may inelastically scatter at least some of the incident electromagnetic radiation 84, thereby generating Raman scattered radiation 88. In one embodiment, the radiation detector 86 may be oriented relative to the radiation source 82 such that the radiation detector 86 collects and receives Raman scattered radiation 88 that is scattered at a substantially right angle relative to the incident electromagnetic radiation 84 through the space between the first layer of Raman signal-enhancing material 42 and the second layer of Raman signal-enhancing material 44. The Raman scattered radiation 88 then can be analyzed to identify or characterize the at least one molecule 18.

Figure 12:
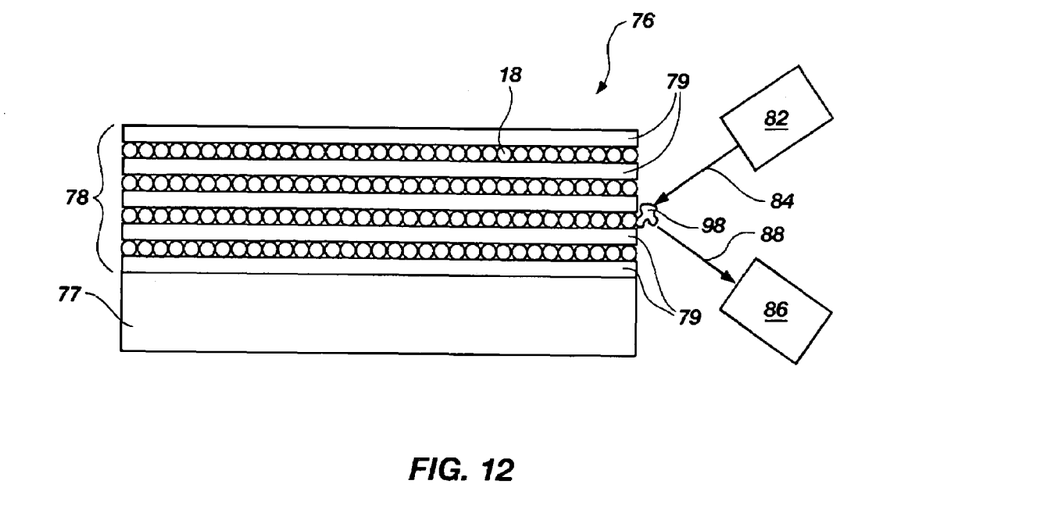
FIG. 12 is a schematic diagram of another Raman system of the present invention that includes the Raman signal-enhancing structure shown in FIG. 10.

The Raman signal-enhancing structure 76 previously described in relation to FIG. 8 is shown in FIG. 12 being irradiated with incident electromagnetic radiation 84 emitted by the radiation source 82. As seen therein, an analyte 98 other than the molecules 18 may be provided proximate or adjacent to a side of the multilayer stack 78 of substantially planar layers of Raman signal-enhancing material 79. The radiation source 82 may be oriented relative to the Raman signal-enhancing structure 76 such that the incident radiation 84 impinges on the Raman signal-enhancing structure 76 at an angle relative to the side of the multilayer stack 78. At least some of the incident electromagnetic radiation 84 may impinge on the analyte 98. The analyte 98 may inelastically scatter at least some of the incident electromagnetic radiation 84, thereby generating Raman scattered radiation 88. In one embodiment, the radiation detector 86 may be oriented relative to the radiation source 82 such that the radiation detector 86 collects and receives Raman scattered radiation 88 that is scattered at a substantially right angle relative to the incident electromagnetic radiation 84. The Raman scattered radiation 88 then can be analyzed to identify or characterize the analyte 98. In this configuration, the molecules 18 may be used to provide a selected, predetermined distance between adjacent layers of Raman signal-enhancing material 79, and the analyte 98 may be positioned on a side of the multilayer stack 78 proximate or adjacent at least two adjacent layers of Raman signal-enhancing material 79 while conducting Raman spectroscopy on the analyte 98.

The structures, systems, and methods described herein may be used to improve the sensitivity of currently available Raman spectroscopy systems and to improve known techniques for performing Raman spectroscopy. The structures and methods described herein allow for the vertical construction, spacing, and positioning of elements or features formed from a Raman signal-enhancing material. By enabling vertical construction of the elements or features, the spacing and location of such elements or features in Raman signal-enhancing structures can be more precisely controlled.

The Raman signal-enhancing structures and Raman spectroscopy systems described herein may be used to perform hyper-Raman spectroscopy and to enhance the hyper-Raman scattered radiation.

The performance of molecular sensors, nanoscale electronics, optoelectronics, and other devices employing the Raman Effect may be improved by using Raman signal-enhancing structures, Raman spectroscopy systems, and methods that embody teachings of the present invention.

Although the foregoing description contains many specifics, these are not to be construed as limiting the scope of the present invention, but merely as providing certain representative embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A Raman signal-enhancing structure comprising:
   a first layer of Raman signal-enhancing material;
   a substantially monomolecular layer of molecules disposed on at least a portion of the first layer of Raman signal-enhancing material;
   a second layer of Raman signal-enhancing material disposed on at least a portion of the substantially monomolecular layer of molecules, the second layer of Raman signal-enhancing material being disposed on a side of the layer of molecules opposite the first layer of Raman signal-enhancing material; and
   a substrate, the first layer of Raman signal-enhancing material being disposed on a surface of the substrate and comprising a plurality of substantially planar islands, each island comprising a Raman signal-enhancing material.

2. The Raman signal-enhancing structure of claim 1, wherein at least one of the first layer of Raman signal-enhancing material and the second layer of Raman signal-enhancing material is discontinuous.

3. The Raman signal-enhancing structure of claim 1, wherein each of the first layer of Raman signal-enhancing material and the second layer of Raman signal-enhancing material are substantially planar.

4. The Raman signal-enhancing structure of claim 3, wherein at least one of the first layer of Raman signal-enhancing material and the second layer of Raman signal-enhancing material has a selected thickness of less than about ten nanometers.

5. The Raman signal-enhancing structure of claim 1, wherein the substantially monomolecular layer of molecules has a thickness of less than about five nanometers.

6. The Raman signal-enhancing structure of claim 1, further comprising a plurality of layers of Raman signal-enhancing material, each layer of Raman signal-enhancing material being separated from adjacent layers of Raman signal-enhancing material by a substantially monomolecular layer of molecules, a thickness of each substantially monomolecular layer of molecules defining a distance separating the layers of Raman signal-enhancing material adjacent thereto.

7. The Raman signal-enhancing structure of claim 1, wherein the second layer of Raman signal-enhancing material comprises a plurality of substantially planar islands, each island comprising a Raman signal-enhancing material.

8. The Raman signal-enhancing structure of claim 7, wherein the first layer of Raman signal-enhancing material comprises a plurality of apertures extending through the first layer of Raman signal-enhancing material and the second layer of Raman signal-enhancing material comprises a plurality of apertures extending through the second layer of Raman signal-enhancing material.

9. The Raman signal-enhancing structure of claim 8, wherein the apertures extending through the first layer of Raman signal-enhancing material are substantially aligned with the apertures extending through the second layer of Raman signal-enhancing material.

10. A Raman system comprising:
    a radiation source;
    a Raman signal-enhancing structure comprising:
       a first layer of Raman signal-enhancing material;
       a substantially monomolecular layer of molecules disposed on at least a portion of the first layer of Raman signal-enhancing material;
       a second layer of Raman signal-enhancing material disposed on at least a portion of the substantially monomolecular layer of molecules, the second layer of Raman signal-enhancing material being disposed on a side of the layer of molecules opposite the first layer of Raman signal-enhancing material; and
       a substrate, the first layer of Raman signal-enhancing material being disposed on a surface of the substrate and comprising a plurality of substantially planar islands, each island comprising a Raman signal-enhancing material; and
    a radiation detector configured to detect Raman scattered radiation.

11. The Raman system of claim 10, wherein the radiation source comprises a laser.

12. The Raman system of claim 10, wherein the radiation detector comprises a wavelength dispersive grating and a charge coupled device.

13. The Raman system of claim 10, wherein at least one of the first layer of Raman signal-enhancing material and the second layer of Raman signal-enhancing material is discontinuous.

14. The Raman system of claim 10, wherein at least one of the first layer of Raman signal-enhancing material and the second layer of Raman signal-enhancing material is substantially planar and has a selected thickness of less than about ten nanometers.

15. The Raman system of claim 10, wherein the substantially monomolecular layer of molecules has a thickness of less than about five nanometers.

16. The Raman system of claim 10, wherein the Raman signal-enhancing structure further comprises a plurality of layers of Raman signal-enhancing material, each layer of Raman signal-enhancing material being separated from adjacent layers of Raman signal-enhancing material by a substantially monomolecular layer of molecules, a thickness of each substantially monomolecular layer of molecules defining a distance separating the layers of Raman signal-enhancing material adjacent thereto.

17. The Raman signal-enhancing structure of claim 10, wherein the second layer of Raman signal-enhancing material comprises a plurality of substantially planar islands, each island comprising a Raman signal-enhancing material.

18. The Raman signal-enhancing structure of claim 17, wherein the first layer of Raman signal-enhancing material comprises a plurality of apertures extending through the first layer of Raman signal-enhancing material and the second layer of Raman signal-enhancing material comprises a plurality of apertures extending through the second layer of Raman signal-enhancing material.

19. The Raman signal-enhancing structure of claim 18, wherein the apertures extending through the first layer of Raman signal-enhancing material are substantially aligned with the apertures extending through the second layer of Raman signal-enhancing material.

* * * * *